United States Patent [19]

Dobrin et al.

[11] Patent Number: 5,441,691
[45] Date of Patent: Aug. 15, 1995

[54] PROCESS FOR MICROAPERATURING AND MICROEMBOSSING A POLYMERIC WEB

[75] Inventors: G. Chris Dobrin; Donna S. Phillips, both of Cincinnati, Ohio

[73] Assignee: The Procter & Gamble Company, Cincinnati, Ohio

[21] Appl. No.: 129,532

[22] Filed: Sep. 30, 1993

[51] Int. Cl.⁶ .................. B29C 59/02; B29C 69/02
[52] U.S. Cl. .................. 264/504; 264/555; 264/557; 264/570; 425/326.1; 425/387.1
[58] Field of Search .......... 264/504, 555, 557, 570; 425/290, 326.1, 387.1, 388

[56] References Cited

U.S. PATENT DOCUMENTS

| | | | |
|---|---|---|---|
| 2,776,451 | 1/1957 | Chavannes | 264/555 |
| 2,776,452 | 1/1957 | Chavannes | 264/555 |
| 3,054,148 | 9/1962 | Zimmerli | 264/504 |
| 3,966,383 | 6/1976 | Bussey, Jr. et al. | 264/555 |
| 4,155,693 | 5/1979 | Raley | 425/290 |
| 4,609,518 | 9/1986 | Curro et al. | 264/504 |
| 4,629,643 | 12/1986 | Curro et al. | 428/131 |
| 4,637,819 | 1/1987 | Ouellette et al. | 604/369 |
| 4,681,793 | 7/1987 | Linman et al. | 428/138 |
| 4,695,422 | 9/1987 | Curro et al. | 264/504 |
| 4,772,444 | 9/1988 | Curro et al. | 264/557 |
| 4,778,644 | 10/1988 | Curro et al. | 264/557 |
| 4,839,216 | 6/1989 | Curro et al. | 428/134 |
| 4,846,821 | 7/1989 | Lyons et al. | 604/369 |
| 4,859,519 | 8/1989 | Cabe, Jr. et al. | 425/290 |

*Primary Examiner*—Catherine Timm
*Attorney, Agent, or Firm*—William Scott Andes; Kevin C. Johnson; John M. Howell

[57] ABSTRACT

A continuous, multi-phase process for microaperturing and microembossing a substantially continuous web of substantially planar polymeric film to conform with the image of multiple forming structures, each having a patterned forming surface with a multiplicity of fine-scale apertures and an opposed surface. Each forming structure is open from the apertures in the forming surface to its opposed surface. The web of film has an indefinite length, a first surface, a second surface and a thickness. The thickness is the distance between the first surface and the second surface. The process includes at least two sequential forming phases, one of which involves aperturing of the web of film to coincide with fine-scale apertures in the first forming structure and another of which involves conformance of the web of film to the profile of the fine-scale apertures in the second forming structure.

18 Claims, 7 Drawing Sheets

PROCESS FOR MICROAPERATURING AND MICROEMBOSSING A POLYMERIC WEB

TECHNICAL FIELD

The present invention relates to a process for microaperturing and microembossing a substantially continuous web of substantially planar polymeric film so as to coincide with the image of one or more forming structures.

BACKGROUND OF THE INVENTION

It has long been known in the disposable absorbent bandage an that it is extremely desirable to construct absorptive devices, such as disposable diapers, sanitary napkins, incontinent briefs, and the like, presenting a dry cloth-like surface feel to the user's skin at any anticipated points of contact, e.g., topsheets and/or backsheets.

While woven and nonwoven fibrous webs are often employed for this purpose because of their pleasant surface feel, polymeric webs have been shown to exhibit more desirable fluid transport and fluid restraining characteristics in many circumstances.

U.S. Pat. No. 4,629,643 issued to Curro et al. on Dec. 16, 1986 discloses a microapertured polymeric web which exhibits a soft and silky tactile impression on at least one surface thereof. The silky feeling surface of the web exhibits a pattern of discrete volcano-like surface aberrations which are not readily discernible to the normal naked eye when the perpendicular distance between the web and the observer's eye is at least about 12 inches. The density of the surface aberrations being at least about 3,600 per square inch, and the center-to-center distance between adjacent surface aberrations does not exceed about 25 mils. Each surface aberration has its amplitude oriented substantially perpendicular to the surface in which said surface aberration originates and exhibits a maximum cross-sectional dimension not exceeding about 20 mils as measured perpendicular to its amplitude. The end of each surface aberration includes at least one microaperture substantially coincidental with its point of maximum amplitude. The microaperture exhibits a multiplicity of thin, irregularly shaped petals about its periphery. The microaperture creates a discontinuity which reduces the resistance to compression and shear of each surface aberration as well as the degree of contact with the observer's skin, whereby the tactile impression of the web is perceived as generally soft and silky.

While the microapertured web of Curro et al. is particularly well suited for use as a backsheet and/or topsheet on a disposable absorbent article, the microapertured web may still give the impression of a plastic web as the portion of the web of film between adjacent microapertures is substantially planar.

Accordingly, it is an object of the present invention to provide a microapertured plastic web which exhibits a soft and silky tactile impression and which exhibits a cloth-like or nonplastic visual appearance.

As used herein the term "microapertured", when used to describe plastic webs, ribbons and films of the present invention, refers to webs, ribbons and films which have been caused to conform to the surface of a three-dimensional forming structure so that both surfaces thereof exhibits a three-dimensional pattern of apertures corresponding to the cross-section of the forming structure, the apertures comprising the pattern not being individually discernible to the normal naked eye when the perpendicular distance between the viewer's eye and the plane of the web is about 12 inches. As used herein the term "microembossed", when used to describe plastic webs, ribbons and films of the present invention, refers to webs, ribbons and films which have been caused to conform to the surface of a three-dimensional forming so that both surfaces thereof exhibit a three-dimensional pattern of surface aberrations corresponding to the cross-section of the forming structure, the surface aberrations comprising the pattern not being individually discernible to the normal naked eye when the perpendicular distance between the viewer's eye and the plane of the web is about 12 inches.

SUMMARY OF THE INVENTION

The present invention pertains, in a particularly preferred embodiment, to a multi-phase method of making microapertured and microembossed polymeric webs. A web of film is continuously supported on a first forming structure exhibiting a multiplicity of fine-scale apertures which place the opposed surfaces of said first forming structure in fluid communication with one another. The first forming structure moves in a direction parallel to the direction of travel of the web of film and carries the web of film in said direction. A first fluid pressure differential is substantially continuously applied across the thickness of the web of film along the direction of movement of the first forming structure which exhibits the fine-scale apertures. The first fluid pressure differential is sufficiently great to cause the web of film to rupture in those areas coinciding with the fine-scale apertures in the first forming structure forming a microapertured web. The aperturing of the web of film is preferably carried out by directing a high pressure liquid jet at the web of film. The microapertured web of film is continuously supported on a second forming structure exhibiting a multiplicity of fine-scale apertures which place the opposed surfaces of the second forming structure in fluid communication with one another. The second forming structure moves in a direction parallel to the direction of travel of the microapertured web of film and carries the microapertured web of film in that direction. A second fluid pressure differential is substantially continuously applied across the thickness of the microapertured web of film along the direction of movement of the second forming structure. The second fluid pressure differential is sufficiently great to cause the microapertured web of film to be urged into substantial conformance with the fine-scale apertures of the second forming structure while substantially maintaining the integrity of the fine-scale apertures formed by the first fluid pressure differential forming a microapertured and microembossed web of film. The microapertured web of film is urged into substantial conformance with the second forming structure by directing a high pressure liquid jet at the microapertured web of film.

Preferably, the microapertured web of film is fed onto the second forming structure so that the surface of the microapertured web of film which contacted the first forming structure does not contact the second forming structure.

The present invention pertains, in a preferred embodiment, to a continuous, multi-phase apparatus for perforating and embossing a substantially continuous web of substantially planar polymeric film to form a microapertured and microembossed polymeric web.

The apparatus includes a first forming structure for continuously supporting the web of film. The first forming structure exhibits a multiplicity of fine-scale apertures which place the opposed surfaces of the first forming structure in fluid communication with one another. The apparatus also includes means for moving the first forming structure in a direction parallel to the direction of travel of the web of film. Means for substantially continuously applying a first fluid pressure differential across the thickness of the web of film along the direction of movement of the first forming structure is also provided. The fluid pressure differential is sufficiently great to cause the web of film to rupture in those areas coinciding with the fine-scale apertures in the first forming structure forming a microapertured web of film. A second forming structure continuously supports the microapertured web of film. The second forming structure exhibits a multiplicity of fine-scale apertures which place the opposed surfaces of the second forming structure in fluid communication with one another. The apparatus includes means for moving the second forming structure in a direction parallel to the direction of travel of the microapertured web of film. A means is provided for substantially continuously applying a second fluid pressure differential across the thickness of the microapertured web of film along the direction of movement of the second forming structure. The second fluid pressure differential is sufficiently great to cause the microapertured web of film to be urged into substantial conformance with the fine-scale apertures of the second forming structure while substantially maintaining the integrity of the fine-scale apertures formed by the first fluid pressure differential.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE PRESENT INVENTION

While the present invention will be described in the context of providing microapertured and microembossed plastic webs particularly suited for use as a backsheet on disposable absorbent articles such as disposable diapers, sanitary napkins, adult incontinent briefs and the like, the present invention is in no way limited to such application. To the contrary, the present invention may be practiced to great advantage whenever it is desired to produce plastic films or webs exhibiting properties, characteristics, aesthetics, fineness of detail, etc., not previously obtainable using prior art web forming processes. The detailed description of the structures disclosed herein and their suggested use as a backsheet in a disposable absorbent article context will allow one skilled in the art to readily adapt the invention to produce webs well suited to other applications.

Figure 1B:
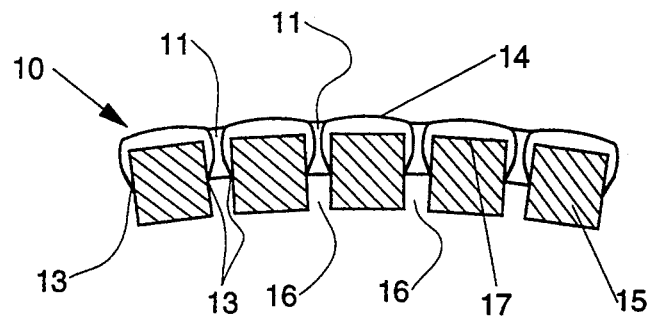
FIG. 1B is a greatly enlarged inset showing, in simplified terms, the condition of the polymeric web after it has been subjected to a first fluid pressure differential on the first forming structure.
Figure 1A:
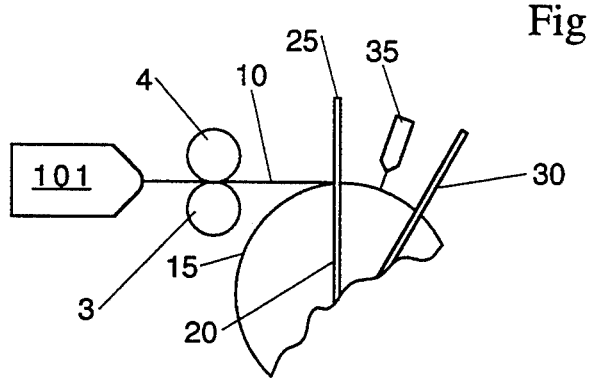
FIG. 1A is a partial illustration of a variation of the process generally shown in FIG. 1, wherein the supply roll of substantial planar polymeric film is replaced by an extruder which extrudes a web of molten resin onto the first forming structure.
Figure 1:
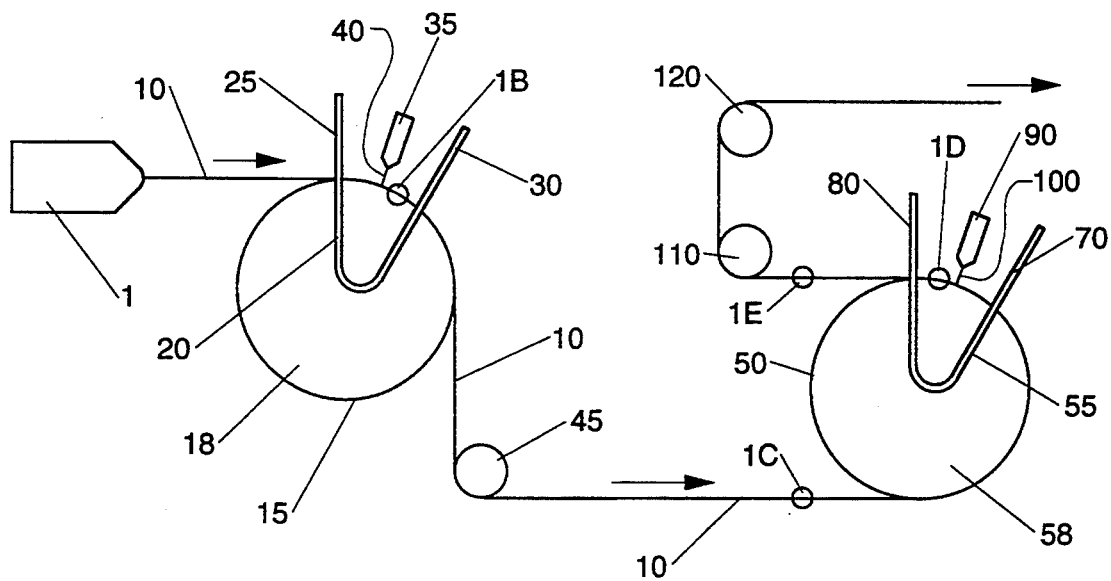
FIG. 1 is a simplified schematic illustration of a two-phase film forming process of the present invention.

A particularly preferred multi-phase, continuous forming process of the present invention is schematically illustrated in FIG. 1. In the embodiment shown in FIG. 1, a web of substantially planar film 10 comprised of a polymeric material such as polyethylene is fed from a supply roll 1 onto the surface of a first forming drum 18 about which a forming structure 15 continuously rotates at substantially the same speed as the incoming web. The forming drum 18 preferably includes an internally located vacuum chamber 20 which is preferably stationary relative to the moving forming structure 15. A pair of stationary baffles 25, 30 approximately coinciding with the beginning and the end of the vacuum chamber 20 are located adjacent the exterior surface of the forming structure. Intermediate the stationary baffles 25, 30 there is preferably provided means for applying a fluid pressure differential to the substantially planar web of polymeric film 10 as it passes across the suction chamber. In the illustrated embodiment, the fluid pressure differential applicator means comprises a high pressure liquid nozzle 35 which discharges a jet of liquid 40, such as water, substantially uniformly across the entire width of the web 10. Details as to the construction, positioning and operating pressure of liquid nozzle 35 are fully set forth in the commonly assigned U.S. Pat. No. 4,695,422 issued to Curro et al. on Sep. 22, 1977, said patent being hereby incorporated herein by reference.

Figure 2:
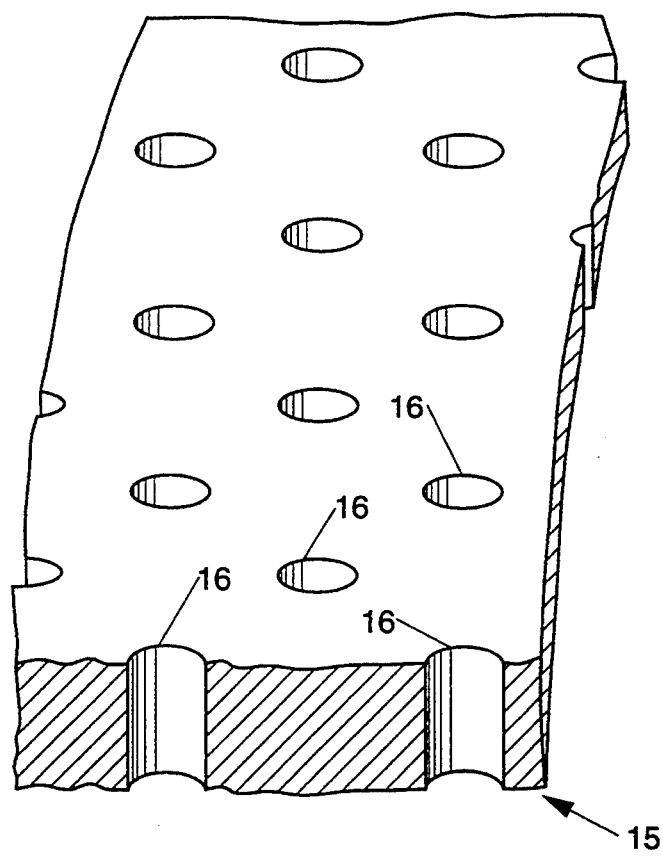
FIG. 2 is a greatly enlarged fragmentary view of the first forming structure utilized to support the polymeric web when the web is subjected to a first fluid pressure differential generally in accordance with the process illustrated in FIG. 1.

Forming structure 15, a greatly enlarged fragmentary segment of which is illustrated in FIG. 2, includes a multiplicity of relatively small apertures 16 across all or any desired portion of its surface. For disposable diaper backsheet applications these apertures typically range in size between about 1 mil and about 10 mils in diameter. Their spacing may be in a regular pattern or it may vary randomly, as desired, in the resultant web. Methods of constructing suitable three-dimensional tubular forming members of this general type are disclosed in commonly assigned U.S. Pat. No. 4,508,256 issued to Radel et al. on Apr. 2, 1985 and commonly assigned U.S. Pat. No. 4,509,908 issued to Mullane, Jr. on Apr. 9, 1985, said patents being hereby incorporated herein by reference.

The apertures 16 in the forming structure 15 may be of any desired shape or cross-section when the forming structure is fabricated utilizing the laminar construction techniques generally disclosed in the aforementioned commonly assigned patents.

Alternatively, the tubular shaped forming structure 15 may be comprised of non-laminar construction and the desired pattern of apertures 16 created by means of laser drilling or the like. It is also possible to use belts or the like comprised of pliable material and operating continuously about a pair of rolls. In the latter circumstance it is generally desirable to provide suitable support beneath the pliable belt when it is subjected to the fluid pressure differential to avoid distortion.

Figure 3:
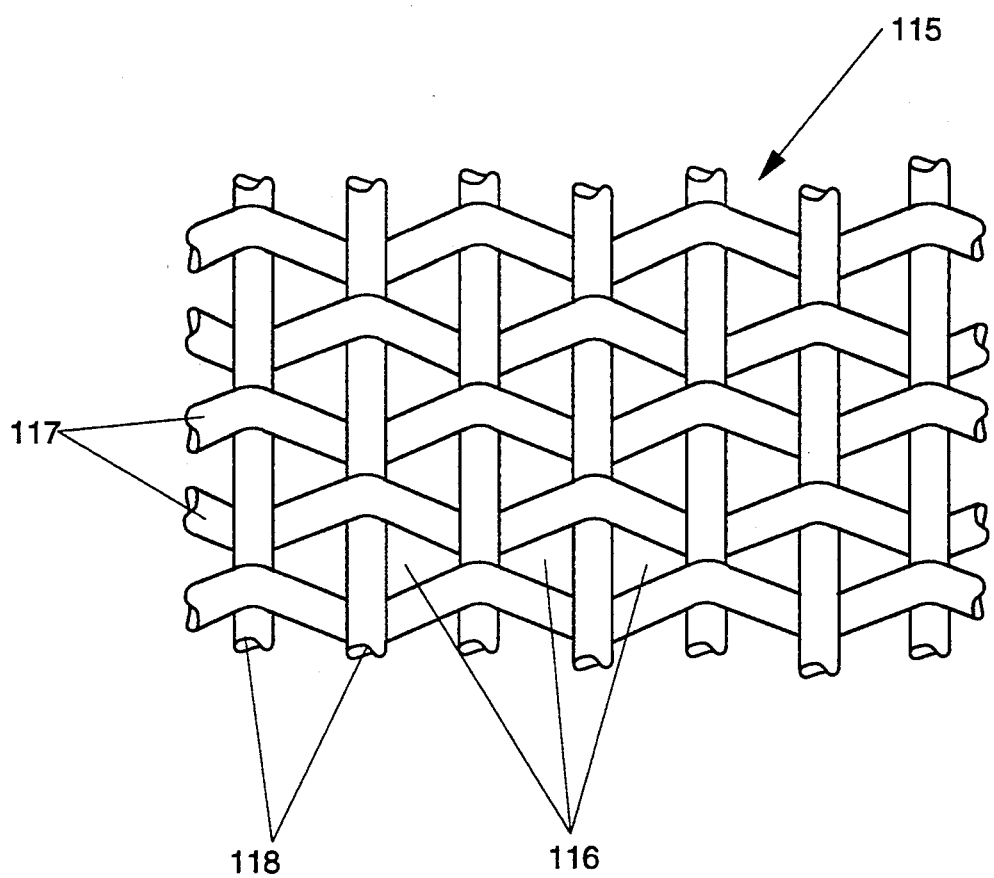
FIG. 3 is a greatly enlarged illustration of a fragment of an alternative forming structure which could be utilized when the polymeric web is subjected to the first fluid pressure differential generally illustrated in FIG. 1.

Still another suitable forming structure which can be used to provide fine-scale aperturing of the polymeric web 10 comprises a woven wire mesh 115 such as that shown in the highly enlarged fragmentary illustration of FIG. 3. In this situation a multiplicity of intersecting filaments 117 and 118 are interwoven with one another to provide a knuckle pattern, such as that generally shown in FIG. 3, about the surface of the forming structure 115. The woven wire mesh filaments may be comprised of metal or polymeric material. Woven wire mesh forming structures 115 having filaments 117, 118 ranging in diameter from about 3 mils to about 7 mils and mesh counts ranging from about 140 by 140 per square inch to about 80 by 80 per square inch, respectively, will typically produce very soft feeling apertured webs when subjected to the high pressure liquid jet 40 issuing from nozzle 35, as generally shown in FIG. 1. The relatively small apertures created in such webs substantially correspond to the void spaces created in the interstices 116 between the intersecting filaments.

As will be appreciated by those skilled in the art, the degree of conformance of the polymeric web 10 to the surface of the forming structure 15 and the size of the apertures created therein will be influenced by factors such as the temperature of the film 10 at the time it is subjected to the liquid jet 40, the pressure at which the jet 40 is applied to the surface of the film, the temperature of the liquid comprising the jet, the mass flux of the liquid jet, etc.

In general, when the fluid pressure differential applied to the web is in the form of vacuum, the higher the temperature of the incoming film 10, the greater will be the degree of conformance and aperturing. However, when the fluid pressure differential applied to the web is in the form of a high pressure liquid jet, as is the case in FIG. 1, it is generally preferred that the incoming web be in a solid rather than a molten state. In the case of the embodiment shown in FIG. 1A, a web of molten resin 10 extruded from a conventional extruder 101 could be fed between a pair of chill rolls 3, 4 prior to being fed onto the forming structure 15 to substantially cool the resin before it passes beneath liquid jet 40.

Whatever the origin of the incoming web of polymeric material 10, after it passes beneath the liquid jet 40, its condition will be generally as shown in the greatly enlarged inset of FIG. 1B. At this point, fine-scale apertures or microapertures 11 corresponding to the relatively small apertures 16 in forming structure 15 have been created in the film 10. The small volcano-like cusps 13 formed about the edge of each microaperture 11 reflect a degree of thinning of the film just prior to rupture.

Figure 1C:
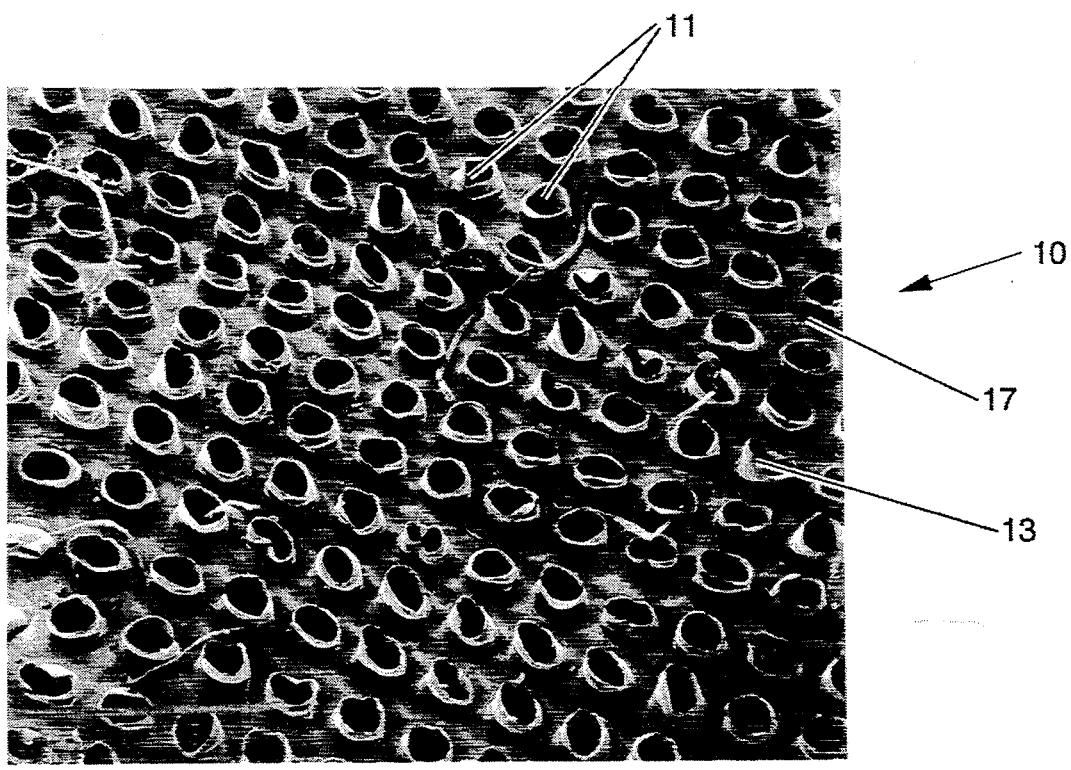
FIG. 1C is a greatly enlarged photograph of the polymeric web after is has been removed from the first forming structure.

Following application of the first fluid pressure differential to the film, the microapertured polymeric web 10 is removed from the surface of the first fine-scale forming structure 15 about an idler roll 45 in the condition shown in greatly enlarged form in the inset of FIG. 1C. Because of the presence of the cusps 13 surrounding each of the microapertures 11, the surface 17 which contacted forming structure 15 exhibits a much softer tactile impression than the surface 14 (not shown) which was contacted by the liquid jet 40. Accordingly, surface 17 of the web is generally preferred as a wearer contacting surface over surface 14.

After completion of the first phase of the web forming process disclosed in FIG. 1, the microapertured web 10 may be fed to the second phase of the forming process for microembossing or to a rewind station for temporary storage. In the latter circumstance, application of the second phase of the process may be deferred until a later date, perhaps at a different location.

Because of the desirable tactile impression imparted to surface 17 of the web 10 in the embodiment illustrated in FIG. 1, a web which is to undergo microembossing is preferably fed onto a second forming structure 50 which operates about forming drum 58 so that its opposite surface 14 is placed in contact with forming structure 50. Forming drum 58, which is generally similar to forming drum 18, also includes a stationary vacuum chamber 55 located adjacent the interior of forming structure 50. Stationary baffles 70 and 80 substantially coincide with the leading and trailing edges of the vacuum chamber 55, thereby defining a second fluid pressure differential zone wherein a second liquid nozzle 90, generally similar to liquid nozzle 35, is positioned. Liquid nozzle 90 also discharges a relatively high pressure liquid jet 100 against the surface 17 of web 10 as it passes therebeneath.

Because forming structure 50 is used to emboss and not aperture the web 10, the pressure and mass flux rates of nozzle 90 are preferably adjusted independently of the pressure and mass flux rates used for nozzle 35. Specifically, the pressure and mass flux rate of nozzle 90 will be lower than the pressure and mass flux rate of nozzle 35 so as to only emboss and not aperture the web of film as it is fed onto the second forming structure 50.

Forming structure 50 includes a multiplicity of relatively small apertures across all or any desired portion of its surface, generally similar to that of forming structure 15. The apertures typically range in size between about 1 mil and about 10 mils in diameter. Their spacing may be in a regular pattern or it may vary randomly, as desired, in the resultant web. A particularly preferred forming structure is a woven wire mesh, similar to the woven wire mesh 115 shown in FIG. 3. The woven wire mesh includes a multiplicity of intersecting filaments interwoven with one another. The filaments range in diameter from about 3 mils to about 7 mils and mesh counts ranging from about 120 by 120 per square inch to about 60 by 60 per square inch, respectively. In a particularly preferred embodiment, the mesh count of the second forming structure 50 will be less than the mesh count of the first forming structure. Preferably, the mesh count of the second forming structure will be at least 20 filaments per square inch less than the mesh count of the first forming structure, more preferably, the mesh count of the second forming structure will be at least about 30 filaments per square inch less than the mesh count of the first forming structure, and most preferably the mesh count of the second forming structure will be at least about 40 filaments per square inch less than the mesh count of the first forming structure. Each of the forming structures produces patterns of microapertures and microembossments, respectively, in the web having a pattern density corresponding to the mesh count of each respective forming structure.

As is more readily apparent from the inset of FIG. 1C, the web of film 10 containing microapertures 11 is fed onto the exterior surface of forming structure 50 such that its surface 14 contacts the forming structure, while its surface 17 is oriented toward fluid nozzle 90. Accordingly, the small cusps of the apertures 11 are oriented toward nozzle 90.

Figure 1E:
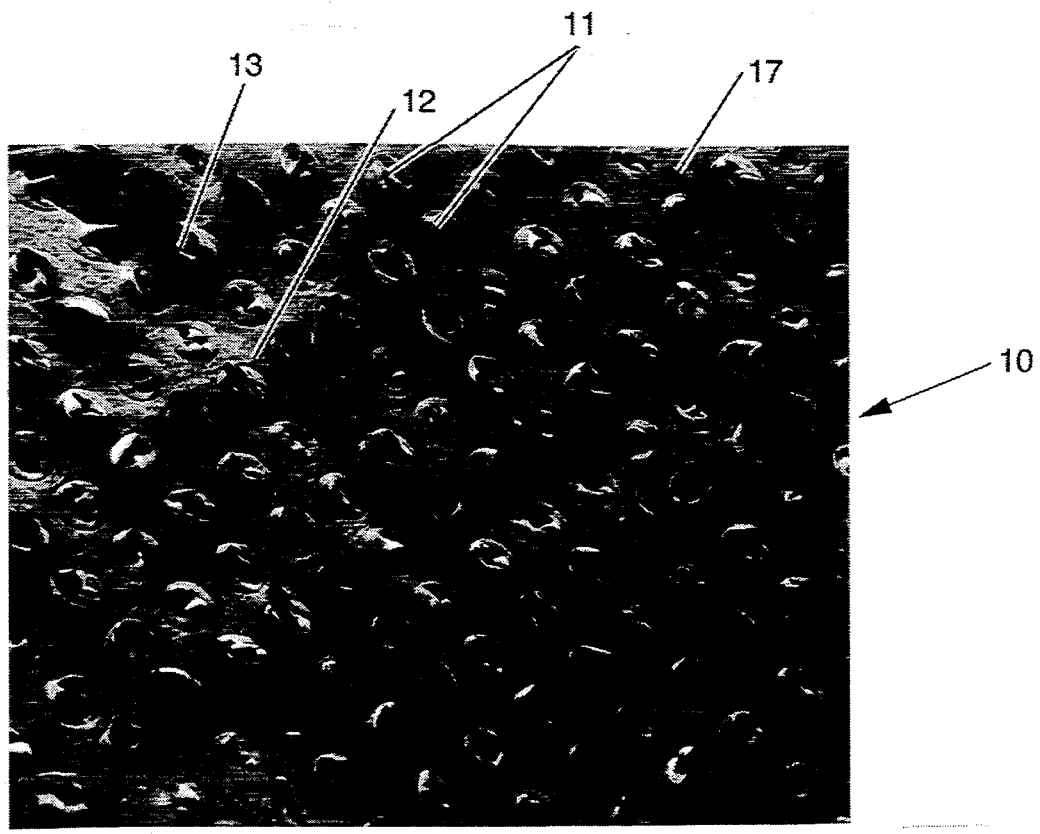
FIG. 1E is a greatly enlarged photograph of the polymeric web after completion of the two-phase forming process generally illustrated in FIG. 1.
Figure 1D:
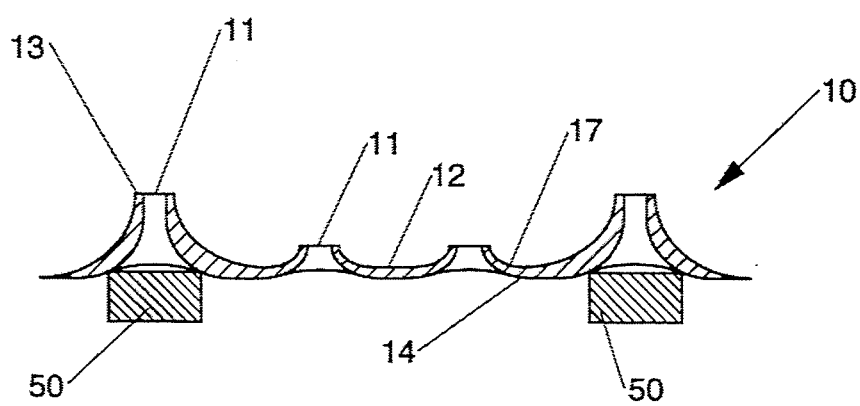
FIG. 1D is a greatly enlarged inset of the polymeric web after it has been fed onto a second forming structure exhibiting a multiplicity of fine-scale apertures so that its opposite surface is in contact with the second forming structure, said polymeric web having thereafter been subjected to a second fluid pressure differential.

The effect produced by fluid nozzle 90 on the web of plastic film 10 as it passes therebeneath is generally illustrated in the greatly enlarged cross-section shown in FIG. 1D. In particular, the web 10 has been caused to assume the microscopic cross-section exhibited by the forming structure 50 without destroying all or a substantial portion of the microapertures 11. As will be appreciated by those skilled in the art, characteristics inherent in the incoming web or characteristics introduced in earlier phases of the present multi-phase forming process are generally preserved whenever the latter phases of the forming operation are carried out while the web is in a solid rather than a molten state. As a result, the web exhibits a multiplicity of microembossments 12.

After completion of the second passing phase the microapertured and microembossed polymeric web 10 is removed from forming structure 50 and wrapped about idler rolls 110 and 120 from whence it may be fed either to a rewinding station for temporary storage or directly to converting lines where it may be applied to making finished product structures, such as disposable absorbent bandages.

As will be apparent from the greatly enlarged photograph of the web shown in FIG. 1E, the fully processed plastic web of film 10 exhibits a pattern of fine-scale apertures or microapertures 11 and a pattern of fine-scale embossments or microembossments 12 superimposed upon the pattern of microapertures. Due to the tactile impression imparted to the web by cusps 13, web 10 is normally perceived as well suited for sustained contact with the skin. Furthermore, the visual impression imparted to the web by microembossments 12 is normally perceived as being cloth-like thereby reducing the perception of plastic which many wearers resist placing in contact with their skin.

Figure 4A:
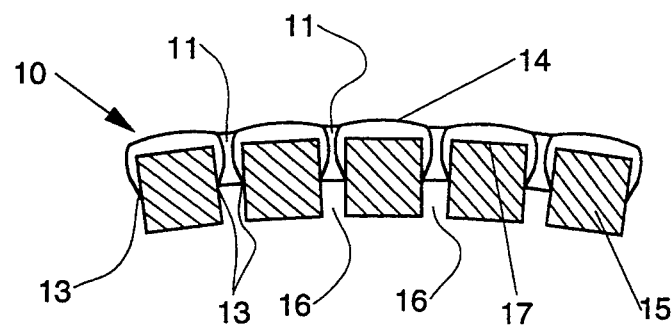
FIG. 4A is a greatly enlarged inset showing the condition of the polymeric web after it has been subjected to a first fluid pressure differential identical to the one illustrated in FIG. 1.
Figure 4B:
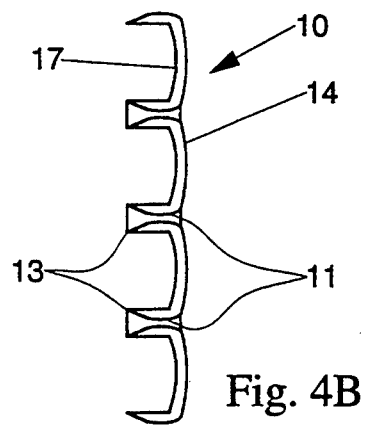
FIG. 4B is a greatly enlarged inset showing the condition of the plastic web after its removal from the first forming structure illustrated in FIG. 1.
Figure 4:
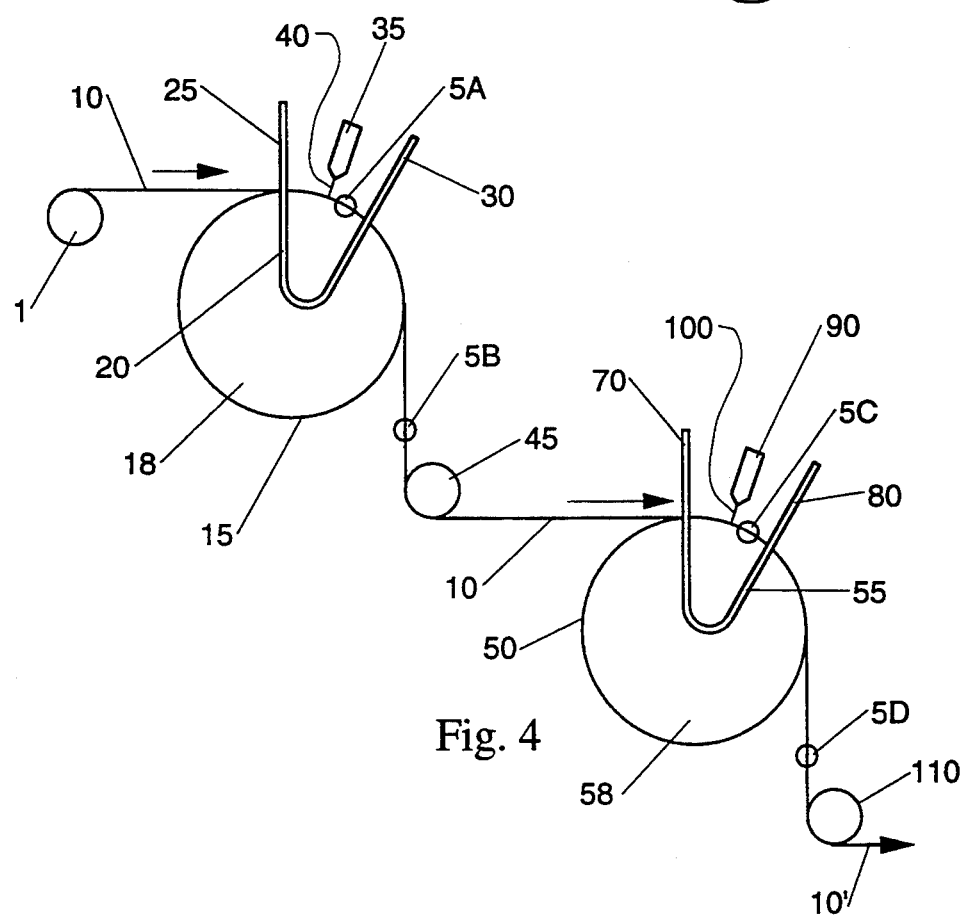
FIG. 4 is a simplified schematic illustration of an alternative two-phase forming process of the present invention.

FIG. 4 is a simplified illustration of an alternative multi-phase polymeric web forming process of the present invention. Like the process generally illustrated in FIG. 1, the process shown in FIG. 4 is carried out in two discrete phases. As can be seen from a comparison of FIGS. 4A and 4B to FIGS. 1B and 1C, respectively, the first phase of the process which provided the fine-scale apertures 11 in the web of film 10 is essentially identical. However, in the embodiment shown in FIG. 4, the web of film is fed directly onto a second forming structure 50, identical to the one shown in FIG. 1, without reverse wrapping of the film. Accordingly, surface 17 is placed in contact with forming structure 50, while surface 14 is placed so that it will be contacted by the liquid jet 100 issuing from fluid nozzle 90.

Figure 4C:
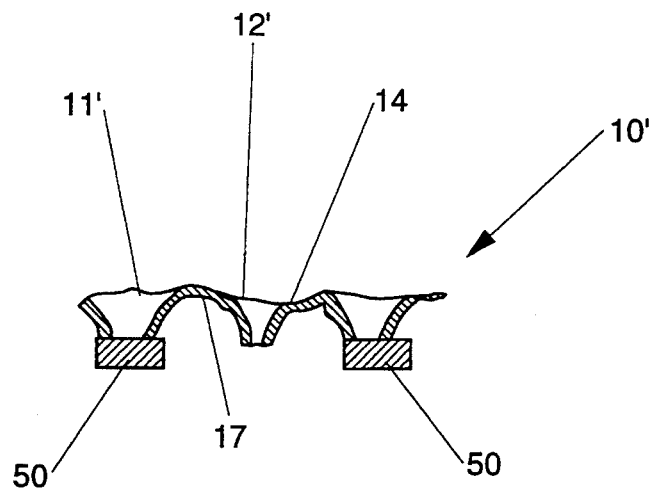
FIG. 4C is a greatly enlarged inset showing the condition of the web after it has been removed from the fist forming structure and fed onto a second macroscopic cross-section forming structure without reversing its orientation, said web having thereafter been subjected to a second fluid pressure differential.

With the exception of reversing the position of stationary baffles 70 and 80 and reversing the direction of rotation of forming structure 50 about forming drum 58, the second phase of the process shown in FIG. 4 is substantially identical with that shown in FIG. 1. The cross-section which results after passage of the web of film under fluid nozzle 90 is generally shown at 10' in FIG. 4C.

After passing beyond stationary baffle 80, the microapertured and microembossed web of film 10 is passed about idler roll 110 and fed either to suitable rewind apparatus for temporary storage or directly to a converting operation for incorporation into the final product in which the web is to be employed.

Figure 4D:
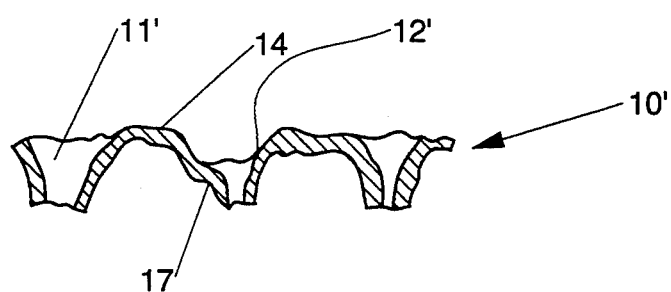
FIG. 4D is a greatly enlarged inset-showing the resultant web after completion of the two-phase forming process generally disclosed in FIG. 4.

The final cross-section of the resultant web 10' is shown after removal from the second forming structure 50 in the greatly enlarged inset of FIG. 4D. The fully processed plastic web of film 10' exhibits a pattern of fine-scale apertures or microapertures 11' and a pattern of fine-scale embossments or microembossments 12'.

As will be appreciated by those skilled in the art, process embodiments of the is present invention which utilize multiple forming structures offer considerable flexibility with respect to the types of characteristics which may be provided in a single microapertured and microembossed plastic web.

As will be appreciated, it is not necessary that the entire surface of a polymeric web be processed in accordance with the present invention. It may, for example, be desirable to microaperture and microemboss the web of film only in discrete predetermined areas.

It is believed that the description contained herein will enable one skilled in the art to practice the present invention in many and varied forms. Nonetheless, the following exemplary embodiments are set forth for purposes of illustration:

EXAMPLE I

A microapertured and microembossed web is made in step-wise fashion, generally following the two stages of the process disclosed in FIG. 1. The input web (10) is polyethylene, 0.001 inches thick (Consolidated Thermoplastics, #24765, Harrington, Del. 19952). This web (10) is fed onto forming structure (15) at a speed of 500 feet per minute and subjected to the high pressure water jet (40). The water temperature is 165° F., the water pressure about 1000 psig, and the water flow about 10 gallons per minute per cross-machine direction inch of web width. The forming structure is a woven wire 120×120 mesh screen, having 0.0037 inch wires. (Cambridge Wire Cloth Co., Cambridge, Md. 21613.) This first stage produces a web containing a multiplicity of small apertures, approximately 0.004 inches in diameter, at a density of 120 such apertures per linear inch in both directions. This finely apertured web is then wound onto a take-up roll. The second stage is carried out by taping a 6 inch by 12 inch portion of the aforementioned finely apertured web onto a different forming structure. This forming structure is a woven wire 60×60 twill weave mesh screen, having 0.0037 inch wires. The finely apertured web is reverse wrapped (small capillary networks oriented toward the second high pressure liquid nozzle) on the latter forming structure and is subjected to a high pressure water jet at a web speed of approximately 500 feet per minute. The water temperature is 120° F., the water pressure was about 300 psig and the water flow was approximately 5 gallons per minute per cross-machine direction inch of web width.

EXAMPLE II

A microapertured and microembossed web is made in step-wise fashion, generally following the two stages of the process disclosed in FIG. 1. The input web (10) is polyethylene, 0.001 inches thick (Consolidated Thermoplastics, #24765, Harrington, Del. 19952). This web (10) is fed onto forming structure (15) at a speed of 500 feet per minute and subjected to the high pressure water jet (40). The water temperature is 165° F., the water pressure about 1000 psig, and the water flow about 10 gallons per minute per cross-machine direction inch of web width. The forming structure is a woven wire 100×100 mesh screen, having 0.0037 inch wires. (Cambridge Wire Cloth Co., Cambridge, Md. 21613.) This first stage produces a web containing a multiplicity of small apertures, approximately 0.004 inches in diameter, at a density of 120 such apertures per linear inch in both directions. This finely apertured web is then wound onto a take-up roll. The second stage is carried out by taping a 6 inch by 12 inch portion of the aforementioned finely apertured web onto a different forming structure. This forming structure is a woven wire 40×40 square weave mesh screen, having 0.0037 inch wires. The finely apertured web is reverse wrapped (small capillary networks oriented toward the second high pressure liquid nozzle) on the latter forming structure and is subjected to a high pressure water jet at a web speed of approximately 500 feet per minute. The water temperature is 120° F., the water pressure was about 300 psig and the water flow was approximately 5 gallons per minute per cross-machine direction inch of web width.

While a number of particularly preferred embodiments in the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. A continuous, multi-phase process for perforating and embossing a substantially continuous web of substantially planar polymeric film to form a microapertured and microembossed polymeric web, said process comprising the steps of:

(a) continuously supporting said web of film on a first forming structure exhibiting a multiplicity of fine-scale apertures which place the opposed surfaces of said first forming structure in fluid communication with one another, said first forming structure moving in a direction parallel to the direction of travel of said web of film and carrying said web of film in said direction, said first forming structure including a woven wire mesh having a predetermined mesh count;

(b) substantially continuously applying a first fluid pressure differential across the thickness of said web of film along said direction of movement of said first forming structure exhibiting said fine-scale apertures, said first fluid pressure differential being sufficiently great to cause said web of film to rupture in those areas coinciding with said fine-scale apertures in said forming structure forming a microapertured web;

(c) continuously supporting said microapertured web of film on a second forming structure exhibiting a multiplicity of fine-scale apertures which place the opposed surfaces of said second forming structure in fluid communication with one another, said second forming structure moving in a direction parallel to the direction of travel of said microapertured web of film and carrying said microapertured web of film in said direction, said second forming structure including a woven wire mesh having a predetermined mesh count, said predetermined mesh count of said second forming structure being at least about 20 filaments per square inch less than said predetermined mesh count of said first forming structure; and (d) substantially continuously applying a second fluid pressure differential across the thickness of said microapertured web of film along said direction of movement of said second forming structure, said second fluid pressure differential being sufficiently great to cause said microapertured web of film to be urged into substantial conformance with the fine-scale apertures of said second forming structure to form a pattern of fine-scale microembossments superimposed upon a pattern of fine-scale microapertures, said pattern of fine-scale microembossments having a pattern density of at least about 20 filaments per square inch less than a corresponding pattern density of said pattern of fine-scale microapertures, while substantially maintaining the integrity of said fine-scaleapertures formed by said first fluid pressure differential forming a microapertured and microembossed web of film.

2. The process of claim 1, wherein said microapertured web of film is fed onto said second forming structure so that the surface of the microapertured web of film which contacted said first forming structure does not contact said second forming structure.

3. The process of claim 2, wherein said microapertured web of film is transferred from said first forming structure to said second forming structure by passing it through a nip formed between said first and second forming structures.

4. The process of claim 1, wherein said aperturing of said web of film is carded out by directing a high pressure liquid jet at said web of film.

5. The process of claim 1, wherein said web of film is urged into substantial conformance with said second forming structure by directing a high pressure liquid jet at said microapertured web of film.

6. The process of claim 1, wherein only a predetermined portion of said web of film is caused to rupture in those areas coinciding with said fine-scale apertures of said first forming structure.

7. The process of claim 1, wherein only a predetermined portion of said microapertured web of film is caused to substantially conform to said second forming structure.

8. The process of claim 1, wherein said web of substantially planar polymeric film is initially formed by extrusion of a resin melt.

9. The process of claim 1, wherein said predetermined mesh count of said second forming structure is at least about 40 filaments per square inch less than said predetermined mesh count of said first forming structure.

10. A continuous, multi-phase apparatus for perforating and embossing a substantially continuous web of substantially planar polymeric film to form a microapertured and microembossed polymeric web, said apparatus comprising:

(a) a first forming structure for continuously supporting said web of film, said first forming structure exhibiting a multiplicity of fine-scale apertures which place the opposed surfaces of said first forming structure in fluid communication with one another, said first forming structure including a woven wire mesh having a predetermined mesh count;

(b) means for moving said first forming structure in a direction parallel to the direction of travel of said web of film;

(c) means for substantially continuously applying a first fluid pressure differential across the thickness of said web of film along said direction of movement of said first forming structure, said fluid pressure differential being sufficiently great to cause said web of film to rupture in those areas coinciding with said fine-scale apertures in said first forming structure forming a microapertured web of film;

(d) a second forming structure for continuously supporting said microapertured web of film, said second forming structure exhibiting a multiplicity of fine-scale apertures which place the opposed surfaces of said second forming structure in fluid communication with one another, said second forming structure including a woven wire mesh having a predetermined mesh count, said predetermined mesh count of said second forming structure being at least about 20 filaments per square inch less than said predetermined mesh count of said first forming structure;

(e) means for moving said second forming structure in a direction parallel to the direction of travel of said microapertured web of film; and (f) means for substantially continuously applying a second fluid pressure differential across the thickness of said microapertured web of film along said direction of movement of said second forming structure, said second fluid pressure differential being sufficiently great to cause said microapertured web of film to be urged into substantial conformance with the fine-scale apertures of said second forming structure to form a pattern of fine-scale microembossments superimposed upon a pattern of fine-scale microapertures, said pattern of fine-scale microembossments having a pattern density of at least about 20 filaments per square inch less than a corresponding pattern density of said pattern of fine-scale microapertures, while substantially maintaining the integrity of said fine-scale apertures formed by said first fluid pressure differential.

11. The apparatus of claim 10, including means for feeding said microapertured web of film onto said second forming structure so that the surface of said microapertured web of film which contacted said first forming structure does not contact said second forming structure.

12. The apparatus of claim 11, wherein said means for feeding said microapertured web of film from said first forming structure to said second forming structure comprises a nip formed between said first and second forming structures.

13. The apparatus of claim 10, wherein said means for applying said first fluid pressure differential across the thickness of said web of film comprises a high pressure liquid jet directed at said web of film.

14. The apparatus of claim 10, wherein said means for applying said second fluid pressure differential across the thickness of said microapertured web of film comprises a high pressure liquid jet directed at said microapertured web of film.

15. The apparatus of claim 13, wherein a vacuum chamber is positioned adjacent the non-web contacting surface of said first forming structure, said vacuum chamber being aligned with said high pressure liquid jet to collect the liquid which penetrates said web of film.

16. The apparatus of claim 14, wherein a vacuum chamber is positioned adjacent the non-web contacting surface of said second forming structure, said vacuum chamber being aligned with said high pressure liquid jet to collect the liquid which is directed at said microapertured web of film.

17. The apparatus of claim 10, including extruder means for initially forming said substantially planar polymeric film from a resin melt.

18. The apparatus of claim 10, wherein said predetermined mesh count of said second forming structure is at least about 40 filaments per square inch less than said predetermined mesh count of said first forming structure.

* * * * *

UNITED STATES PATENT AND TRADEMARK OFFICE
CERTIFICATE OF CORRECTION

PATENT NO. : 5,441,691

DATED : August 15, 1995

INVENTOR(S) : G. Chris Dobrin and Donna S. Phillips

It is certified that error appears in the above-identified patent and that said Letters Patent is hereby corrected as shown below:

In Col. 1, line 15, "an" should read --art--.

In Col. 10, line 40, "fine-scaleapertures" should read --fine-scale apertures--.

In Col. 10, line 54 (appears to be line 55 compared with the PTO line numbers as printed on the patent), "carded" should read --carried--.

Signed and Sealed this

Nineteenth Day of November, 1996

Attest:

BRUCE LEHMAN

Attesting Officer     Commissioner of Patents and Trademarks